United States Patent [19]

Sauerbier et al.

[11] Patent Number: 5,158,776
[45] Date of Patent: Oct. 27, 1992

[54] SOLID ORAL DOSAGE FORMS OF IFOSFAMIDE

[75] Inventors: Dieter Sauerbier, Werther; Jürgen Engel, Alzenau; Eckhard Milsmann; Klaus Molge, both of Bielefeld; Otto Isaac, Hanau, all of Fed. Rep. of Germany

[73] Assignee: Asta Medica Aktiengesellschaft, Fed. Rep. of Germany

[21] Appl. No.: 733,756

[22] Filed: Jul. 24, 1991

[30] Foreign Application Priority Data

Aug. 3, 1990 [DE] Fed. Rep. of Germany ....... 4024683

[51] Int. Cl.$^5$ .......................... A61K 9/52; A61K 9/48
[52] U.S. Cl. .................... 424/451; 424/463; 424/458; 424/474; 424/482
[58] Field of Search ............... 424/464, 465, 452, 463, 424/458, 451, 474, 482

[56] References Cited

U.S. PATENT DOCUMENTS

| 4,379,038 | 4/1983 | Uaetsu et al. | 204/159.12 |
| 4,929,607 | 5/1990 | Scheffler et al. | 514/110 |
| 4,952,575 | 8/1990 | Sauerbrer et al. | 514/110 |
| 5,019,385 | 5/1991 | Mitsuhashi et al. | 424/85 |

Primary Examiner—Thurman K. Page
Attorney, Agent, or Firm—Cushman, Darby & Cushman

[57] ABSTRACT

Solid oral ifosfamide formulations comprising a capsule containing a mass which consists essentially of the active substance ifosfamide and microcrystalline cellulose, or in the form of tablets which contain, in relation to one part by weight of ifosfamide, 0.1-1.0 parts by weight of tribasic calcium phosphate and
0.04-0.4 parts by weight of polyethylene glycol as well as in addition, related to the weight of the tablet
5-60% by weight of a filling and flow regulating agent
1-10% by weight of a disintegrant
0.1-10% by weight of an antiadhesion agent and
0.1-80% by weight of a binding agent.

7 Claims, No Drawings

SOLID ORAL DOSAGE FORMS OF IFOSFAMIDE

BACKGROUND OF THE INVENTION

Ifosfamide is the INN designation for 3-(2-chloroethyl) -2-(chloroethylamino)-tetrahydro-2H-1,3, 2-oxazophosphorin-2-oxide. Ifosfamide is an important cytostatically active medication of the oxazaphosphorin type.

Ifosfamide is a white crystalline powder with a melting point of 48° C. to 51° C. and has strongly hygroscopic properties. Ifosfamide begins to sinter below the melting point and therefore has to be stored at temperatures that are as low as possible. It is also desirable to avoid contact with humidity whenever possible. Although ifosfamide dissolves to an extent of about 10 percent by weight in water, it is of only limited stability in aqueous solution. Hitherto ifosfamide has only been registered in formulations for parenteral use. Ifosfamide is available in the form of a sterile crystallizate which is dispensed in injection bottles in dosages of 200 mg to 2000 mg. Prior to administration, the sterile crystallizate must be dissolved in water for injection purposes, but it is required that the concentration not exceed 4%. This solution is suitable for intravenous injection. For purposes of short intravenous infusion the ifosfamide solution is dissolved in 500 ml Ringer's solution or similar injection fluids. The duration of infusion is about 30 minutes, possibly 1 to 2 hours. In the case of the 24-hour infusion, the ifosfamide solution is, for example, dissolved in a total of 3 liters of 5% dextrose-sodium chloride solution.

There are many problems associated with the manufacture and processing of ifosfamide. The manufacture of sterile crystallized ifosfamide produces a of changing physical characteristic. The variations on the free-flowing characteristics has a particularly deleterious effect on dosage accuracy when dispensing into injection vials.

The processing of ifosfamide is further impaired by its hygroscopicity and low melting point During longer storage periods the sterile crystallizate sinters and the speed of dissolution decreases. As ifosfamide begins to sinter, the clarity of the solution which can be obtained from it, and the pH value of the solution decrease and a yellow discoloration develops The medication then is generally no longer useful for therapeutic purposes.

Apart from the difficulties in manufacturing the sterile crystallizate, there are, above all, also serious disadvantages in use. Parenteral administration can only be performed by specialized medical personnel. The patient has to be admitted to hospital as an inpatient or must at least attend hospital every day for treatment. This involves a great deal of time on the part of staff and patient and added expense.

The potential danger of the substance necessitates extensive protective measures for the staff during the manufacture of the sterile injection solution from the dry substance. Parenteral therapy is unpleasant for a patient since he has to submit to a painful puncture during application and is connected to an infusion apparatus for the duration of the infusion.

Because of all these disadvantages there has long been a need for an oral dosage form which eliminates the above disadvantages. Oral administration could permit ambulatory therapy. Oral administration of ifosfamide would be pleasant for the patient and would no longer constitute a risk for the medical personnel.

All attempts to develop a solid oral dosage form have, however, failed because of the above-described physical-chemical properties of ifosfamide. In particular it was not possible to prepare a medicinal form in soft gelatin capsules. The active substance appears to react with the capsule wall, becomes tanned and the capsule no longer dissolves in the gastric juices. Similarly, many attempts to develop a tablet have hitherto failed. The substance adhered to the die of the tabletting machine, the tablets were too soft and the active substance sometimes spurted in liquefied form from the mold during compressing.

SUMMARY OF THE INVENTION

It has now surprisingly been found that ifosfamide can be filled into hard gelatin capsules in a mixture with microcrystalline cellulose. It is surprising to note that there is then no deleterious interaction between ifosfamide and the capsule wall. Although the capsule wall contains 12% to 15% of water (weight/weight) and although ifosfamide is both hygroscopic and moisture sensitive, the filled hard gelatin capsule proves capable of being stored for several years. After nlany years, storage, the capsule wall still dissolves in the gastric juice within a few minutes.

For example, the ifosfamide capsules of the present invention contain between 100 mg and 800 mg, preferably between 200 mg and 500 mg of ifosfamide.

The materials dispensed into the capsule consist essentially of ifosfamide and microcrystalline cellulose: they may optionally contain small amounts of conventional flow regulators and antiadhesion agents. These flow regulators and antiadhesion agents may be used singly or in a mixture. The total amount of such additional flow regulating agents and antiadhesion agents, related to 1 part by weight of ifosfamide, is, for example, 0.001 to 0.1 parts by weight, preferably 0.01 to 0.04 parts by weight. It is, for example possible to use flow regulators and antiadhesion agents that are listed in the following textbooks:

W. A. Ritschel, DIE TABLETTE, Editio Cantor Verlag, page 125, 1st edition 1966

Sucker, Fuchs, Speiser, PHARMAZEUTISCHE TECHNOLOGIE, G. Thieme Verlag, Stuttgart, page 334 to 336, 1st edition 1978

M/ nzel, Büchi, Schultz, GALENISCHES PRAKTIKUM, Wissenschaftliche Verlagsgesellschaft Stuttgart, page 731, 1st edition 1959

R. Voigt, LEHRBUCH DER PHARMAZEUTISCHEN TECHNOLOGIE, 4th edition, Verlag Chemie, Weinheim, page 195, 1st edition 1982

P. H. List, ARZNEIMITTELLEHRE, Wissenschaftliche Verlagsanstalt, Stuttgart, page 86, 1st edition 1976

Substances that are particularly suitable are magnesium stearate as well as other stearates, highly disperse silicon dioxide, stearic acid, talcum and polyglycols (for example with molecular weights of 4000 to 6000).

Flow regulating agents that may preferably be used are 0.002 to 0.02 parts by weight, in particular 0.005 to 0.008 parts by weight per 1 part by weight of ifosfamide and, as antiadhesion agents, 0.004 to 0.08 parts by weight, in particular 0.016 to 0.032 parts by weight of ifosfamide.

Moreover the capsules may optionally also contain fillers such as starch, cellulose, lactose, fructose, saccharose, mannitol, sorbitol, calcium phosphate, binding agents such as gelatin, cellulose, pectins, alginates, polyvinylpyrrolidone, disintegrants such as alginates, carboxymethyl celluloses, polyvinylpyrrolidones, ultraamylopectin.

Flow regulating agents that may in particular be used are highly disperse silicon dioxide (for example, Aerosil ® such as Aerosil ® V 200) as well as magnesium stearate.

The amount of microcrystalline cellulose in the capsule of the invention generally amounts to 0.2 to 4 parts by weight, preferably 0.25 to 1 part by weight, in particular 0.3 to 0.35 parts by weight, related to 1 part by weight of ifosfamide.

The microcrystalline cellulose should display a crystallinity index measure[1] between 0.5 to 0.9, for example 0.7.

[1] Crystallinity index is understood to be the quotient of the crystalline portion and the sum of crystalline and amorphous portion. For crystalline cellulose of a grain size of ca. 50 μm the index value is for example 0.71.

The degree of polymerization of the microcrystalline cellulose is for example in the range of 200 to 300. In addition, the microcrystalline cellulose used in accordance with the invention should for example have a mean grain size of ca. 50 μm or under 50 μm. This may be for example under 40 μm. In particular the mean grain size may be 20 μm. Avicel ® is preferably used as microcrystalline cellulose, for example Avicel ® with a grain size spectrum of less than 38 μm (Avicel ® PH 105) (that is at least 90% of the microcrystalline celluloses have a mean particle size smaller than 38 μm, in particular 20 μm).

In addition it was also surprisingly possible to manufacture tablets with the active substance ifosfamide, the combination of tricalcium phosphate and polyethylene glycol being of special importance. By this means, it is now possible for the first time to effect pressing on a conventional tablet press.

Because of its physical properties, the substance ifosfamide cannot be pressed into tablets in a conventional manner using a tabletting machine. All attempts to press the active substance using known auxiliary substances such as for example microcrystalline cellulose, lactose, starch, talcum, highly disperse silicon dioxide and calcium hydrogen phosphate have failed. All attempts using conventional granulation techniques or a fluidized air bed did not lead to tablet masses which could be processed in a perfect manner. In each case the mass adhered very greatly to the die or mold during the pressing process.

In accordance with the present invention, these difficulties are overcome with a tableting formulation which contains, related to one part by weight of ifosfamide:

0.1-1.0 parts by weight of tribasic calcium phosphate and 0.04 to 0.4 parts by weight of polyethylene glycol (for example molecular weight 4000 to 6000) as well as, related to the tablet weight 5-60% by weight of a filling and flow regulating agent
1-10% by weight of a disintegrant
0.1-10% by weight of an antiadhesion agent and
0.1-80% by weight of a binding agent.

In accordance with the invention use is for example made, per 1 part by weight of ifosfamide, of: 0.1-1.0 parts by weight, preferably 0.2-0.5, in particular 0.25-0.30 parts by weight of tribasic calcium phosphate. Related to the tablet mixture, the amount of tricalcium phosphate is for example 3.5 to 35% by weight, preferably 7 to 17.8% by weight, in particular 9 to 11% by weight.

The amount of polyethylene glycol is for example 0.04 to 0.4 parts by weight, preferably 0.1-0.2, in particular 0.13 to 0.15 parts by weight per 1 part by weight of ifosfamide. It is in particular possible to consider polyethylene glycol with molecular weight of 4000 to 6000, preferably polyethylene glycol 6000. Related to the tablet mixture, the amount of polyethylene glycol is for example 1 to 14.0% by weight, preferably 3.5 to 7.5% by weight, in particular 4.5 to 7 or also 4.5 to 6% by weight. The weight ratio of tribasic calcium phosphate to polyethylene glycol is for example 1:0.5.

The following are in addition also contained in the tablet of the invention:

Fillers and flow regulating agents in an amount of 5 to 60% by weight, related to the tablet weight.

Fillers that may for example be considered are starches, celluoses, lactose, saccharose, fructose, sorbitol, mannitol, calcium phosphate, calcium carbonate, calcium sulphate, magnesium carbonate or magnesium oxide. 5-50% by weight are used, related to the tablet weight.

Flow regulating agents that may for example be considered are microcrystalline cellulose, lactose, polyglycols, starches, celluloses, talcum, talcum siliconisatum, calcium arachinate or calcium stearate, cetyl alcohol, stearyl alcohol, myristyl alcohol, stearic acid, lauric acid. Should the flow regulating agent not also serve as a filler, 0.5-10% by weight are used hereof, related to the tablet weight.

Disintegrants: use is for example made of alginates, starches (corn starch), pectins, carboxymethyl celluloses, polyvinylpolypyrrolidone, ultraamylopectin, betonite. 1-10% by weight are used, related to the tablet weight.

Antiadhesion agents: use is for example made of glycols, talcum, talcum siliconisatum, talcum stearinicum, calcium stearate, aluminium stearate, stearic acid. 0.1-10% by weight are used, related to the tablet weight.

Binding agents: for example gelatin, cellulose ethers, amyloses pectins, cellulose, dextrose, polyglycols, tragacanth. Use is made of 0.1-80% by weight, related to the tablet weight.

In particular the tablet of the invention contains the following substances, apart from ifosfamide, tribasic calcium phosphate and polyethylene glycol: microcrystalline cellulose 0.2-1.2 parts by weight, preferably 0.4-1.0, in particular 0.70 - 0.90 parts by weight, related to one part by weight of ifosfamide or related to the tablet weight 7 to 43, preferably 15 to 35% by weight;

lactose 0.15-1.0 parts by weight, preferably 0.24-0.68, in particular 0.30-0.40 parts by weight, related to one part by weight of ifosfamide or related to the tablet weight 5.0 to 36, preferably 8.5 to 25% by weight;

corn starch 0.02-0.24 parts by weight, preferably 0.05-0.20, in particular 0.1-0.15 parts by weight, related to one part by weight of ifosfamide or related to the tablet weight 0.7 to 8.5, preferably 2.0 to 6.5% by weight[ talcum 0.02-0.30 parts by weight, preferably 0.06-0.20, in particular 0.07-0.09 parts by weight, related to one part by weight of ifosfamide or related to the tablet weight 0.70 to 10, preferably 2 to 6.5% by weight;

magnesium stearate 0.004–0.2 parts by weight, preferably 0.02–0.12, in particular 0.035–0.05 parts by weight, related to one part by weight of ifosfamide or related to the tablet weight 0.1 to 7.2, preferably 0.7 to 4.5% by weight.

Tablets as well as capsules may be provided with a coating in known manner. It is possible to apply water-soluble, swellable, water insoluble or gastric juice resistant coatings which nlay be applied to the tablets or capsules from aqueous dispersion or solution or also from solution or dispersion in organic solvents such as for example ethanol, isopropanol, acetone, ether, dichloromethane, methanol.

The capsules and tablets may be manufactured at, for example, between 15° C. and 20° C., preferably between 18° C. and 22° C. The relative humidity in the production rooms should not exceed 40%.

The process for the production of the inventive solid oral ifosfamide formulations is characterized in that between 15° C. and 30° C. either 1 part by weight of the active substance ifosfamide and 0.1–4, preferably 0.2–4, particularly 0.25–1 parts by weight of microcrystalline cellulose and optionally small amounts of conventional flow regulation and antiadhesion agents are homogeneously mixed and filled into capsules or one part by weight of ifosfamide and 0.1–1.0 parts by weight of tribasic calcium phosphate and
0.04–0.4 parts by weight of polyethylene glycol as well as in addition
0.15–2 preferably 0.5–1.5, particularly 1–1.3 parts by weight of a filling and flow regulation agent
0.03–0.5 preferably 0.05–0.4, particularly 0.08–0.2 parts by weight of a disintegrant
0.003–0.5 preferably 0.01–0.4, particularly 0.05–0.2 parts by weight of an antiadhesion agent and
0.003–3 preferably 0.01–2, particularly 0.1–1 parts by weight of a binding agent are homogeneously mixed and then pressed into tablets and optionally the so obtained capsules and tablets respectively are provided with an usual coating.

DETAILED DESCRIPTION OF PREFERRED EMBODIMENTS

The invention is illustrated by the following examples:

EXAMPLE 1

Ifosfamide capsule mass

In accordance with the invention, the capsule mass is for example manufactured according to the following method:

For 12,000 capsules of 250 mg each, 3.0 kg ifosfamide, 1.002 mg microcrystalline cellulose and 0.018 kg highly disperse silicon dioxide are, for example, passed through a 0.8 mm sieve and then mixed in a suitable mixer for 4 minutes. 0.06 kg of magnesium stearate are then added to this mixture (sieved through a 0.8 mm sieve) and mixing is repeated for 1 minute. The finished capsule mass is then dispensed with a capsule machine fitted with size 1 molds into size 1 hard gelatin capsules so that each capsule contains ca. 340 mg of the capsule mass.

For 20,000 capsules of 500 mg each, 10.0 kg ifosfamide, 3.34 kg microcrystalline cellulose and 0.06 kg highly disperse silicon dioxide are for example passed through a 0.8 mm sieve and then mixed in a suitable mixer for 4 minutes-0.2 kg of magnesium stearate are then added to this mixture (sieved through a 0.8 mm sieve) and mixing repeated for 1 minute. The finished capsule mass is then filled in a capsule machine fitted with size 00 molds into size 00 hard gelatin capsules so that each capsule contains ca. 680 mg of the capsule mass. The microcrystalline cellulose is used for example in the form of Avicel PH 105. Avicel PH 105 has a special grain size spectrum and is a flowing substance with good binding and flowing properties.

To manufacture gastric juice resistant capsules, a coating suspension in organic solvent (ifosfamide) is for example applied to 2500 size 1 capsules containing 250 mg ifosfamide. The 3000 g of suspension contain: 1440 g anionic polymerizate of methacrylic acid and methacrylic acid esters with a mean molecular weight of for example 150,000, to which a conventional softener has been added, 18 g of 1,2-propandiol, 36 g of magnesium stearate and 1506 g of isopropanol.

The copolymerizate of methacrylic acid and methylmethacrylate that may for example be considered is Eudragit L ®, in particular in the form of a 12.5% solution in isopropanol (Eudragit L ®/12.5%). Copolymerizates for this type are soluble in neutral to weakly alkaline medium through salt formation with alkalis.

EXAMPLE 2

Ifosfamide tablets

The composition of a tablet containing 250 mg of active substance is for example: One 700 g tablet contains:

| | |
|---|---|
| ifosfamide | 250 mg |
| tribasiccalciumphosphate, fine | 70 mg |
| microcrystalline cellulose | 200 mg |
| lactose | 85 mg |
| polyglycol 6000 | 35 mg |
| corn starch | 30 mg |
| talcum | 20 mg |
| magnesium stearate | 10 mg |

To manufacture the tablet mass for 1500 tablets, 375 g ifosfamide, 105 g tribasic calcium phosphate (fine), 300 g microcrystalline cellulose, 127.5 g lactose, 52.5 g polyglycol 6000, 45 g cornstarch and 30 g talcum are passed through a sieve of mesh size 0.8 mm and mixed for 15 minutes in a suitable mixer. 15 g of magnesium stearate (also sieved) are added and mixing continued for 2 minutes. The tablet mass is then pressed into tablets on a suitable tablet press.

To manufacture tablets with a gastric juice resistant coating, 500 g of an aqueous dispersion as described below are for example applied to 1050 g of tablets:

100 g of the aqueous dispersion contain:

| | |
|---|---|
| polyglycol 6000 | 1.600 g |
| titanium dioxide | 1.100 g |
| iron oxide, yellow | 0.156 g |
| talcum | 4.000 g |
| dimethylpolysiloxane | 0.100 g |
| Eudragit L ® 30 D[2] | 55.000 g |
| water | 38.044 g |
| | 100.000 g |

[2]Eudragit L ® 30 D is the aqueous dispersion of a copolymerisate of an anionic nature based on methacrylic acid and ethyl acrylate. The ratio of the free carboxyl groups to the ester groups is about 1:1. The mean molecular weight is 250,000.

2 Eudragit L ® 30 D is the aqueous dispersion of a copolymerisate of an anionic nature based on methacrylic acid and ethyl acrylate. The ratio of the free carboxyl groups to the ester groups is about 1:1. The mean molecular weight is 250.000.

Conventionally used apparatus, in which the solution or dispersion agent is continuously removed through drying, is for example used to spray on the film solution.

What is claimed is:

1. Solid oral ifosfamide formulations comprising a member of the group consisting of ifosfamide capsules having a capsule mass consisting essentially of the active substance ifosfamide and microcrystalline cellulose having a degree of crystallinity of 0.5–0.9 and ifosfamide tablets containing, for each part by weight of ifosfamide:

0.1–1.0 parts by weight of tribasic calcium phosphate
   0.04–0.4 parts by weight of polyethylene glycol as well as, related to the weight of the tablet:
   5–60% by weight of a filing and flow regulating agent
   1–10% by weight of a disintegrant
   0.1–10% by weight of an antiadhesion agent and
   0.1–80% by weight of a binding agent.

2. An ifosfamide capsule according to claim 1 including conventional flow regulating and antiadhesion agents.

3. An ifosfamide tablet as set forth in claim 1.

4. A process for the production of a solid oral ifosfamide formulation which comprises homogeneously mixing, at 15° C.–30° C., 1 part by weight of the active substance ifosfamide and 0.1–4 parts by weight of microcrystalline cellulose having a degree of crystallinity of 0.5–0.9, and optionally small amounts of conventional flow regulating and antiadhesion agents, and dispensing the resulting mixture into capsules.

5. A process as set forth in claim 4 including applying a coating to the capsules.

6. A process for the production of a solid oral ifosfamide formulation which comprises homogeneously mixing one part of ifosfamide and 0.1–1.0 parts by weight of tribasic calcium phosphate
   0.04–0.4 parts by weight of polyethylene glycol as well as, in addition,
   0.15–2 parts by weight of a filling and flow regulating agent
   0.03–0.5 parts by weight of a disintegrant
   0.003–0.5 parts by weight of an antiadhesion agent and
   0.003–3 parts by weight of a binding agent, and pressing the resulting mixture into tablets.

7. A process as set forth in claim 6 including applying a coating to the tablets.

* * * * *